United States Patent [19]

Jerzewski et al.

[11] Patent Number: 5,006,344
[45] Date of Patent: Apr. 9, 1991

[54] FOSINOPRIL TABLET FORMULATIONS

[75] Inventors: Robert L. Jerzewski, East Millstone; Thomas M. Wong; Lewis J. Gryziewicz, both of North Brunswick; Nemichand B. Jain, Monmouth Junction; Ajit B. Thakur, East Brunswick, all of N.J.

[73] Assignee: E. R. Squibb & Sons, Inc., Princeton, N.J.

[21] Appl. No.: 543,639

[22] Filed: Jun. 26, 1990

Related U.S. Application Data

[63] Continuation-in-part of Ser. No. 377,683, Jul. 10, 1989, abandoned.

[51] Int. Cl.$^5$ .............................................. A61K 9/20
[52] U.S. Cl. ................................... 424/465; 424/456; 424/464; 424/488; 424/490; 424/494
[58] Field of Search ............... 424/456, 488, 494, 464, 424/465; 514/970

[56] References Cited

U.S. PATENT DOCUMENTS

| 4,337,201 | 6/1982 | Petrillo, Jr. | 548/413 |
| 4,384,123 | 5/1983 | Petrillo, Jr. | 548/409 |
| 4,793,998 | 12/1988 | Murthy et al. | 424/440 |
| 4,803,081 | 2/1989 | Falk | 424/488 |
| 4,832,957 | 5/1989 | Dempski | 424/469 |
| 4,900,755 | 2/1990 | Dempski | 424/469 |

OTHER PUBLICATIONS

Holzer et al., "Evaluation of Some Lubricants by the Comparison of Friction Coefficients and Tablet Properties", Acta Pharm. Suec., vol. 18, pp. 139–148 (1981).
Holzer et al., "Evaluation of Sodium Stearyl Fumarate as a Tablet Lubricant", Int. Journ. of Pharmaceutics, vol. 2, 145–153 (1979).
Lindberg, "Evaluation of Some Tablet Lubricants", Acta Pharm. Suec., vol. 9, pp. 207–214 (1972).
Shah et al., "Evaluation of Two New Lubricants . . . ", Drug Development and Industrial Pharmacy, vol. 12, pp. 1329–1346 (1986).
Chowhan et al., "Drug-Excipient Interactions . . . ", Jour. of Pharmaceutical Sciences, vol. 75, pp. 542–545 (1986).

Primary Examiner—Thurman K. Page
Assistant Examiner—D. Gabrielle Phelan
Attorney, Agent, or Firm—Stephen B. Davis

[57] ABSTRACT

Shelf stable tablets containing fosinopril sodium are prepared by employing either sodium stearyl fumarate or hydrogenated vegetable oil as the lubricant. The tablets can contain conventional excipients such as fillers, binders, and disintegrants as well as an optional diuretic.

24 Claims, No Drawings

FOSINOPRIL TABLET FORMULATIONS

RELATED APPLICATION

This application is a continuation-in-part of Ser. No. 377,683 filed July 10, 1989, now abandoned.

BACKGROUND OF THE INVENTION

The sodium salt of fosinopril, (4S)-4-cyclohexyl-1-[[[(RS)-1-hydroxy-2-methylpropoxy](4-phenylbutyl)-phosphinyl]acetyl]-L-proline, propionate (ester) sodium salt, is currently undergoing clinical evaluation as an antihypertensive agent.

Fosinopril, its ability to inhibit the angiotensin converting enzyme and thus lower blood pressure in humans, and formulations of fosinopril including combinations with various diuretics are described by Petrillo, Jr., in U.S. Pat. Nos. 4,337,201 and 4,384,123.

SUMMARY OF THE INVENTION

This invention is directed to the discovery that the shelf life and stability of fosinopril sodium formulated as tablets is increased when the lubricant employed is sodium stearyl fumarate or hydrogenated vegetable oil as compared to tablets employing magnesium stearate as the lubricant. In addition to the fosinopril sodium, the tablet formulation can also include a diuretic, preferably chlorthalidone, a filler, a disintegrant, a binder, a lubricant, and other commonly employed pharmaceutically acceptable agents. The tablet can include a color agent or the tablets can be color film coated. The tablets can be prepared in a variety of shapes and can be scored for the convenience of the user.

DETAILED DESCRIPTION OF THE INVENTION

Fosinopril sodium having the chemical formula

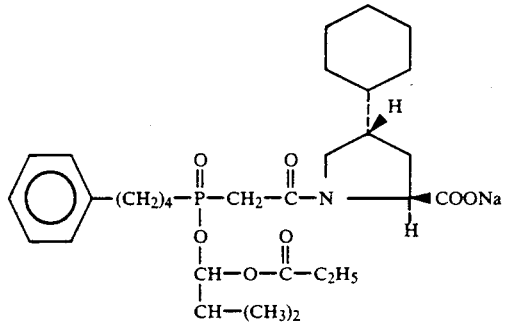

is an angiotensin converting enzyme inhibitor currently being clinically evaluated as an antihypertensive agent.

Fosinopril sodium bulk material has a relatively low bulk density, exhibits poor flow characteristics, and adheres to metal surfaces during tableting. Previously, fosinopril sodium was tableted by a wet granulation process in which the tablet binder material was added to a solvent to form a solution of about 20% on a weight to weight basis. The fosinopril sodium and a portion of the tablet filler and disintegrant were then added. The mix was granulated and dried to less than 1% by weight of volatiles. The remainder of the tablet excipients were added and the final blend was obtained by lubrication with magnesium stearate. It was found that tablets produced from this blend were moisture sensitive and only marginally stable. In order to have a useful shelf life these tablets required the use of a protective package.

This invention is directed to the discovery that by eliminating magnesium stearate as the lubricant during the tableting of fosinopril sodium and instead employing either sodium stearyl fumarate or hydrogenated vegetable oil, tablets having improved stability are obtained. The tablets thus prepared are significantly less moisture sensitive and have a useful shelf life without the need for protective packaging. Sodium stearyl fumarate is the preferred lubricant since hydrogenated vegetable oil can cause processing problems of sticking to the punch tips during long tableting runs.

As discussed by Petrillo, Jr. in U.S. Pat. Nos. 4,337,201 and 4,384,123, various diuretics can be combined with fosinopril sodium for the treatment of hypertension. Suitable diuretics include chlorthalidone, the thiazide diuretics such as chlorothiazide, hydrochlorothiazide, flumethiazide, bendroflumethiazide, etc., ethacrynic acid, ticrynafen, furosemide, musolimine, bumetanide, triameterene, amiloride, spironolactone, and salts thereof with chlorthalidone and hydrochlorothiazide being preferred.

Tablets prepared according to this invention contain from about 5 mg. to about 50 mg. of fosinopril sodium as the sole active agent or from about 10 mg. to about 75 mg. of a combination of fosinopril sodium and diuretic in a ratio of from about 1:5 to about 5:1 on a weight basis.

As discussed above, in addition to the actives, fosinopril sodium and the optional diuretic, and the lubricant, tablets prepared according to this invention will include excipients such as a filler, a disintegrant, and a binder. The preferred filler is lactose or lactose and microcrystalline cellulose. The preferred disintegrants are selected from sodium carboxymethyl starch, cross linked sodium carboxymethyl starch, crospovidone, i.e., 1-ethenyl-2-pyrrolidinone homopolymer, cross linked sodium carboxymethylcellulose (AcDiSol or Croscarmellose Sodium), sodium starch glycolate, and mixtures thereof. The preferred binders are selected from povidone, i.e., 2-pyrrolidinone, 1-ethenyl-, homopolymer, hydroxypropyl cellulose, and mixtures thereof. Alternatively, a single agent such as pregelatinzed starch can be employed as both disintegrant and binder. Other ingredients commonly employed in tableting pharmaceutical products can also be included such as coloring agents.

On a weight percentage basis, the above ingredients will preferably be present in the final tablets as follows:

| Ingredient | Preferred percentage by weight |
| --- | --- |
| Fosinopril sodium | about 1 to about 25 |
| diuretic, (preferably chlorthalidone or hydrochlorothiazide) | from 0 up to about 25 |
| filler (preferably lactose or lactose combined with microcrystalline cellulose) | about 30 to about 90 |
| disintegrant (preferably sodium carboxymethyl starch and its cross linkaged form and/or crospovidone and/or crosslinked sodium carboxymethylcellulose and/or sodium starch glycolate) | about 2 to about 10 |
| binder (preferably | about 1 to about 5 |

-continued

| Ingredient | Preferred percentage by weight |
|---|---|
| povidone and/or hydroxypropyl cellulose) combined binder and disintegrant (preferably pregelatinized starch) | about 5 to about 15 |
| lubricant (preferably sodium stearyl fumarate) | about 0.3 to about 4 |

The fosinopril sodium tablets of this invention can be prepared by conventional tablet forming techniques such as, for example, wet granulation and dry granulation. In the wet granulation process, the active ingredient or ingredients are mixed with portions of the filler and disintegrant. This blend is then wet granulated with a solution of the binder in a solvent. The solution will preferably be from about 5% to 20% by weight of solvent and the preferred solvents include ethanol, isopropanol, and water. The resultant wet granulation is then dried and milled. The dried granulation is then mixed with the balance of the filler and disintegrant. The resulting blend is mixed with sodium stearyl fumarate, which is preferred, or hydrogenated vegetable oil to produce the final mix which is then compressed into tablets.

In the dry granulation process, the active ingredient or ingredients and the filler, disintegrant and binder are blended in a mixer (planetary or high shear) for several minutes. The blend is then milled and mixed with sodium stearyl fumarate, which is preferred, or hydrogenated vegetable oil to produce the final mix which is then compressed into tablets.

The wet granulation process employing water as the solvent and the dry granulation process have the added advantage of avoiding the use of an organic solvent. This results in a cost savings as well as a safer process needing fewer environmental controls.

EXAMPLE 1

Tablets were prepared containing:

| Ingredient | Weight (mg.) |
|---|---|
| Fosinopril sodium | 40.0 |
| Chlorthalidone | 15.0 |
| Lactose | 318.00 |
| Povidone | 9.0 |
| Crospovidone | 14.0 |
| Sodium stearyl fumarate | 4.0 |
| Water | q.s. |
| Tablet weight | 400 |

100,000 tablets of the above formulation were prepared as follows. A blend was prepared of fosinopril sodium (4000 g.), chlorthalidone (1500 g.), lactose (17,900 g.), and crospovidone (700 g.) in a suitable mixer such as planetary mixer or high shear mixer for 5 to 10 minutes. Povidone (900 g.) was dissolved in water (7 liters) and the above blend was wet granulated with the entire povidone solution. The wet granulation was dried at 45°–70° C. in a suitable dryer such as a tray drying oven or a fluid bed dryer until the volatile content of the wet granulation was less than 3% by weight. The dried granulation was passed through a hammer mill fitted with 0.03–0.07 inch screen operating at medium to fast speed, knives forward. The screened granulation was then mixed with lactose (13,900 g.) and crospovidone (700 g.) in the mixer (planetary or high shear) for 5 to 10 minutes. Sodium stearyl fumarate (400 g.) was then added to the above blend and mixing was continued for 1 to 3 minutes. The final blend was then compressed into 400 mg. tablets using a rotary tablet press.

EXAMPLES 2 TO 5

Following the procedure of Example 1, the following tablets were obtained.

| | Weight (mg.) | | | |
|---|---|---|---|---|
| Ingredient | 2 | 3 | 4 | 5 |
| Fosinopril sodium | 20.0 | 10.0 | 5.0 | 5.0 |
| Chlorthalidone | 15.0 | 15.0 | 25.0 | 5.0 |
| Lactose | 244.75 | 161.0 | 62.5 | 82.5 |
| Povidone | 6.75 | 4.5 | 3.0 | 3.0 |
| Crospovidone | 10.50 | 7.5 | 3.5 | 3.5 |
| Sodium stearyl fumarate | 3.0 | 2.0 | 1.0 | 1.0 |
| Water | q.s. | q.s. | q.s. | q.s. |
| Tablet weight | 300 | 200 | 100 | 100 |

EXAMPLES 6 TO 9

Following the procedure of Examples 1 to 5, the following tablets were obtained.

| | Weight (mg.) | | | |
|---|---|---|---|---|
| Ingredient | 6 | 7 | 8 | 9 |
| Fosinopril sodium | 20.0 | 10.0 | 20.0 | 10.0 |
| Hydrochlorthiazide | 12.5 | 12.5 | 12.5 | 12.5 |
| Lactose | 237.5 | 157.5 | 112.5 | 123.5 |
| Avicel (Microcrystalline cellulose | — | — | 40.0 | 40.0 |
| Povidone | 6.0 | 4.0 | 4.0 | 4.0 |
| Croscarmellose Sodium (cross linked sodium carboxymethylcellulose) | 15.0 | 10.0 | — | — |
| Sodium starch glycolate | — | — | 7.0 | 7.0 |
| Sodium stearyl fumarate | 9.0 | 6.0 | 4.0 | 3.0 |
| Water | q.s. | q.s. | q.s. | q.s. |
| Tablet weight | 300 | 200 | 200 | 200 |

EXAMPLES 10 AND 11

The following tablets were prepared by a modification of the procedures of Examples 1 to 9.

| | Weight (mg.) | |
|---|---|---|
| Ingredients | 10 | 11 |
| Fosinopril sodium | 20.0 | 10.0 |
| Hydrochlorothiazide | 12.5 | 12.5 |
| Lactose | 107.5 | 118.5 |
| Avicel (microcrystalline cellulose) | 40.00 | 40.00 |
| Pregelatinized starch | 16.0 | 16.0 |
| Sodium stearyl fumarate | 4.0 | 3.0 |
| Water | q.s. | q.s. |
| Tablet weight | 200 | 200 |

In the preparation of the tablets of Examples 10 and 11, a portion of the pregelatinized starch was added before the wet granulation step and the remainder was added to the dried granulation.

EXAMPLE 12

Tablets were prepared containing the following:

| Ingredient | Weight (mg.) |
| --- | --- |
| Fosinopril sodium | 5.0 |
| Lactose | 139.5 |
| Avicel (microcrystalline cellulose) | 40.0 |
| Crospovidone | 7.0 |
| Povidone | 4.5 |
| Sodium stearyl fumarate | 4.0 |
| Alcohol (used for processing, not present in tablet) | q.s. |
| Tablet Weight | 200 |

200,000 tablets of the above formulation were prepared as follows. Fosinopril sodium (1,000 g.), lactose (16,500 g.), Avicel (1,000 g.) and crospovidone (700 g.) were mixed in a suitable mixer (planetary or high shear) for 5 to 10 minutes. Povidone (800 g.) was dissolved in denatured alcohol (4 liters) and blended with the above mixture forming a wet granulate. This wet granulate was dried at 45°-70° C. in suitable dryer such as a tray drying oven or a fluid bed dryer until the volatile content of the wet granulation was less than 3% by weight. The dried granulation was passed through a hammer mill fitted with a 0.03-0.07 inch screen operating at medium to fast speed, knives forward. The screened granulation was mixed with lactose (12,100 g.), Avicel (7,000 g.) and crospovidone (700 g.) in a suitable mixer (planetary or high shear) for 5 to 10 minutes. Sodium stearyl fumarate was added to the above blend and mixed for 1 to 3 minutes in the same mixer. This final blend was then compressed into 200 mg. tablets using a rotary tablet press.

EXAMPLE 13 AND 14

Following the procedure of Example 12, the following tablets were obtained.

| | Weight (mg.) | |
| --- | --- | --- |
| Ingredient | 13 | 14 |
| Fosinopril sodium | 10.0 | 20.0 |
| Lactose | 134.5 | 124.5 |
| Avicel (microcrystalline cellulose) | 40.0 | 40.0 |
| Crospovidone | 7.0 | 7.0 |
| Povidone | 4.5 | 4.5 |
| Sodium stearyl fumarate | 4.0 | 4.0 |
| Alcohol (used for processing, not present in tablet) | q.s. | q.s. |
| Tablet Weight | 200 | 200 |

EXAMPLE 15

Tablets were prepared containing the following:

| Ingredient | Weight (mg.) |
| --- | --- |
| Fosinopril sodium | 5.0 |
| Lactose | 143 |
| Avicel (microcrystalline cellulose) | 40.0 |
| Crospovidone | 7.0 |
| Povidone | 4.0 |
| Sodium stearyl fumarate | 1.0 |
| Tablet weight | 200 mg. |

200,000 tablets of the above formulation were prepared as follows. Fosinopril sodium (1,000 g.), lactose (28,600 g.), Avicel (8,000 g.), crospovidone (1400 g.) and povidone (800 g.) were mixed in a suitable mixer (planetary or high shear) for 5 to 10 minutes. The blend was then passed through a hammer mill equipped with a 0.04-0.08 inch size round hole screen operating at medium speed, knives forward. Sodium stearyl fumarate (200 g.) was added to the above blend and mixed for 1 to 3 minutes in the same mixer. This final blend was then compressed into 200 mg. tablets using a rotary tablet press.

Following the procedures of Examples 1 to 5 and 12 to 15, similar tablets were prepared substituting hydrogenated vegetable oil for the sodium stearyl fumarate.

EXAMPLE 16

Following the procedure of Example 12 fosinopril sodium tablets were prepared utilizing sodium stearyl fumarate, hydrogenated vegetable oil, and magnesium fumarate as the lubricant. The initial amount of fosinopril sodium was measured and similar measurements were made after 10 days and 25 days storage under varying conditions.

| | Weight of Fosinopril Sodium | | |
| --- | --- | --- | --- |
| Storage condition | Sodium stearyl fumarate formulation | Hydrogenated vegetable oil formulation | Magnesium stearate formulation |
| Initial | 4.99 mg. | 4.86 mg. | 4.95 mg. |
| 10 days at 75° C. in closed containers | 4.36 mg. | 4.71 mg. | 3.44 mg. |
| 10 days at 50° C., 75% relative humidity in open containers | 4.87 mg. | 4.60 mg. | 3.44 mg. |
| 10 days at 60° C., 75% relative humidity in open containers | 4.36 mg. | 3.92 mg. | 0.90 mg. |
| 25 days at 75° C., in closed containers | 4.25 mg. | 4.37 mg. | 3.39 mg. |
| 25 days at 50° C., 75% relative humidity in open containers | 4.69 mg. | 4.31 mg. | 1.83 mg. |

What is claimed is:

1. A stable tablet comprising on a weight percentage basis from about 1% to about 25% fosinopril sodium, up to about 25% of a diuretic, from about 30% to about 90% of a filler, from about 2% to about 10% of a disintegrant, from about 1% to about 5% of a binder, or from about 5% to about 15% of a single agent which is both binder and disintegrant, and from about 0.3% to about 4% of a lubricant selected from the group consisting of sodium stearyl fumarate and hydrogenated vegetable oil.

2. The tablet of claim 1 wherein said lubricant is sodium stearyl fumarate.

3. The tablet of claim 2 wherein said filler is lactose or a blend of lactose and microcrystalline cellulose, said disintegrant is selected from the group consisting of sodium carboxymethyl starch, cross linked sodium carboxymethyl starch, crospovidone, cross linked sodium carboxymethylcellulose, sodium starch glycolate, and mixtures thereof, said binder is selected from the group consisting of povidone, hydroxypropyl cellulose, and mixtures thereof, and said single agent which is both binder and disintegrant is pregelatinized starch.

4. The tablet of claim 3 containing from about 1% to about 25% by weight of chlorthalidone.

5. The tablet of claim 4 wherein said filler is lactose, said disintegrant is crospovidone, and said binder is povidone.

6. The tablet of claim 5 containing on a weight percentage basis about 10% fosinopril sodium, about 3.75% chlorthalidone, about 79.5% lactose, about 2.25% povidone, about 3.5% crospovidone, and about 1% sodium stearyl fumarate.

7. The tablet of claim 5 containing on a weight percentage basis about 6.67% fosinopril sodium, about 5% chlorthalidone, about 81.58% lactose, about 2.25% povidine, about 3.5% crospovidone, and about 1% sodium stearyl fumarate.

8. The tablet of claim 5 containing on a weight percentage basis about 5% fosinopril sodium, about 7.5% chlorthalidone, about 80.5% lactose, about 2.25% povidone, about 3.75% crospovidone, and about 1% sodium stearyl fumarate.

9. The tablet of claim 5 containing on a weight percentage basis about 5% fosinopril sodium, about 25% chlorthalidone, about 62.5% lactose, about 3.0% povidone, about 3.5% crospovidone, and about 1% sodium stearyl fumarate.

10. The tablet of claim 5 containing on a weight percentage basis about 5% fosinopril sodium, about 5% chlorthalidone, about 82.5% lactose, about 3% povidone, about 3.5% crospovidone, and about 1% sodium stearyl fumarate.

11. The tablet of claim 3 wherein the only active ingredient is fosinopril sodium.

12. The tablet of claim 11 wherein said filler is a mixture of lactose and microcrystalline cellulose, said disintegrant is crospovidone, and said binder is povidone.

13. The tablet of claim 12 containing on a weight percentage basis about 2.5% fosinopril sodium, about 69.75% lactose, about 20% microcrystalline cellulose, about 3.5% crospovidone, about 2.25% povidone, and about 2% sodium stearyl fumarate.

14. The tablet of claim 12 containing on a weight percentage basis about 5% fosinopril sodium, about 67.25% lactose, about 20% microcrystalline cellulose, about 3.5% crospovidone, about 2.25% povidone, and about 2% sodium stearyl fumarate.

15. The tablet of claim 12 containing on a weight percentage basis about 10% fosinopril sodium, about 62.25% lactose, about 20% microcrystalline cellulose, about 3.5% crospovidone, about 2.25% povidone, and about 2% sodium stearyl fumarate.

16. The tablet of claim 12 containing on a weight percentage basis about 2.5% fosinopril sodium, about 71.5% lactose, about 20% microcrystalline cellulose, about 3.5% crospovidone, about 2% povidone, and about 0.5% sodium stearyl fumarate.

17. The tablet of claim 3 containing from about 1% to about 25% by weight of hydrochlorothiazide.

18. The tablet of claim 17 wherein said filler is lactose or a blend of lactose and microcrystalline cellulose, said disintegrant is cross linked sodium carboxymethylcellulose or sodium starch glycolate, said binder is povidone, and said single agent which is both binder and disintegrant is pregelatinized starch.

19. The tablet of claim 18 containing on a weight percentage basis about 6.6% fosinopril sodium, about 4.2% hydrochlorothiazide, about 79.2% lactose, about 2.0% povidone, about 5.0% cross linked sodium carboxymethylcellulose, and about 3.0% sodium stearyl fumarate.

20. The tablet of claim 18 containing on a weight percentage basis about 5.0% fosinopril sodium, about 6.25% hydrochlorothiazide, about 78.75% lactose, about 2.0% povidone, about 5.0% cross linked sodium carboxymethylcellulose, and about 3.0% sodium stearyl fumarate.

21. The tablet of claim 18 containing on a weight percentage basis about 10.0% fosinopril sodium, about 6.25% hydrochlorothiazide, about 56.25% lactose, about 20.0% microcrystalline cellulose, about 2.0% povidone, about 3.5% sodium starch glycolate, and about 2.0% sodium stearyl fumarate.

22. The tablet of claim 18 containing on a weight percentage basis about 5.0% fosinopril sodium, about 6.25% hydrochlorothiazide, about 61.75% lactose, about 20.0% microcrystalline cellulose, about 2.0% povidone, about 3.5% sodium starch glycolate, and about 1.5% sodium stearyl fumarate.

23. The tablet of claim 18 containing on a weight percentage basis about 10.0% fosinopril sodium, about 6.25% hydrochlorothiazide, about 53.75% lactose, about 20.0% microcrystalline cellulose, about 8.0% pregelatinized starch, and about 2.0% sodium stearyl fumarate.

24. The tablet of claim 18 containing on a weight percentage basis about 5.0% fosinopril sodium, about 6.25% hydrochlorothiazide, about 59.25% lactose, about 20.0% microcrystalline cellulose, about 8.0% pregelatinized starch, and about 1.5% sodium stearyl fumarate.

* * * * *